(12) United States Patent
Bottcher et al.

(10) Patent No.: US 9,005,978 B2
(45) Date of Patent: Apr. 14, 2015

(54) DETECTION OF THE INTEGRITY OF A TIGHT, CLOSED, SOFT PLASTIC POUCH FOR RECEIVING AND PROTECTING A PRODUCT OR A BIOPHARMACEUTICAL DEVICE

(75) Inventors: Lars Bottcher, Melsungen (DE); Martin Dahlberg, Bovenden (DE)

(73) Assignee: Sartorius Stedim FMT SAS, Aubagne (FR)

( * ) Notice: Subject to any disclaimer, the term of this patent is extended or adjusted under 35 U.S.C. 154(b) by 230 days.

(21) Appl. No.: 13/876,612

(22) PCT Filed: Aug. 22, 2011

(86) PCT No.: PCT/FR2011/051942
§ 371 (c)(1),
(2), (4) Date: Mar. 28, 2013

(87) PCT Pub. No.: WO2012/042139
PCT Pub. Date: Apr. 5, 2012

(65) Prior Publication Data
US 2013/0210153 A1  Aug. 15, 2013

(30) Foreign Application Priority Data
Sep. 30, 2010 (FR) ..................... 10 57930

(51) Int. Cl.
*G01N 31/22* (2006.01)
*G01N 21/78* (2006.01)
*B65D 75/38* (2006.01)
(Continued)

(52) U.S. Cl.
CPC ................. *G01N 21/783* (2013.01); *A61J 1/14* (2013.01); *B65D 75/38* (2013.01); *B65D 79/02* (2013.01); *B65D 81/2084* (2013.01);
(Continued)

(58) Field of Classification Search
CPC .... B65D 75/38; B65D 79/02; B65D 81/2061; B65D 81/2084; G01N 21/783; A61L 2/26; A61L 2202/181; A61J 1/14
USPC ........ 206/569, 534, 438, 459.1, 807; 436/1, 3
See application file for complete search history.

(56) References Cited

U.S. PATENT DOCUMENTS

| 4,098,577 A | 7/1978 | Halpern |
| 4,434,893 A | 3/1984 | Barlow |

(Continued)

FOREIGN PATENT DOCUMENTS

| EP | 1012073 B1 | 3/2002 |
| FR | 2 252 619 A | 11/1974 |

(Continued)

*Primary Examiner* — Arlen Soderquist
(74) *Attorney, Agent, or Firm* — Young & Thompson

(57) ABSTRACT

A pouch (2) includes: a first, inner, envelope (1) which is closed, delimiting a first space (6) forming a pouch stricto sensu (1) intended for receiving a biopharmaceutical product or device; a second, outer, envelope (8) which is closed, delimiting a second space (9) in which is located the first envelope/pouch stricto sensu (1); a spacer element (11); at least one tracer gas located in the first space (6) or in the intermediate space (14) at a partial pressure different from that of the intermediate space or of the first space; and at least one colorimetric detection layer (12), responding to the concentration of tracer gas which reaches it by changing from a first color to a second color, and being an integral part of a wall (3, 4) of the first envelope/defined pouch (1) and/or of a wall (13) of the second envelope and/or of the spacer element.

17 Claims, 4 Drawing Sheets

(51) Int. Cl.
  *B65D 79/02*   (2006.01)
  *B65D 81/20*   (2006.01)
  *A61L 2/26*    (2006.01)
  *A61J 1/14*    (2006.01)

(52) U.S. Cl.
  CPC .............. *B65D 81/2061* (2013.01); *A61L 2/26* (2013.01); *A61L 2202/181* (2013.01)

(56) References Cited

U.S. PATENT DOCUMENTS

| | | | |
|---|---|---|---|
| 4,436,203 A | | 3/1984 | Reyner |
| 4,755,405 A | * | 7/1988 | Massucco et al. ............ 428/35.7 |
| 4,813,541 A | | 3/1989 | Velasco et al. |
| 4,872,553 A | * | 10/1989 | Suzuki et al. ............... 206/524.4 |
| 5,217,118 A | * | 6/1993 | Mochizuki et al. ......... 206/524.2 |
| 5,219,524 A | | 6/1993 | Evans, II |
| 5,228,573 A | * | 7/1993 | Pavelle et al. .............. 206/459.1 |
| 5,407,829 A | * | 4/1995 | Wolfbeis et al. ................... 436/1 |
| 5,439,648 A | * | 8/1995 | Balderson et al. .............. 422/86 |
| 5,458,896 A | * | 10/1995 | Porter ............................ 426/232 |
| 5,503,835 A | * | 4/1996 | Van Roekel ................... 424/404 |
| 5,617,812 A | * | 4/1997 | Balderson et al. ............. 116/206 |
| 6,050,400 A | * | 4/2000 | Taskis et al. ................... 206/204 |
| 6,076,457 A | | 6/2000 | Vallot |
| 6,186,932 B1 | | 2/2001 | Vallot |
| 6,196,056 B1 | | 3/2001 | Ewing et al. |
| 6,399,387 B1 | * | 6/2002 | Stenholm et al. ................... 436/1 |
| 6,689,438 B2 | * | 2/2004 | Kennedy et al. ............. 428/36.6 |
| 6,892,567 B1 | | 5/2005 | Morrow |
| 6,905,016 B2 | * | 6/2005 | Kanios et al. ................. 206/204 |
| 7,017,391 B2 | * | 3/2006 | Klein et al. ..................... 73/40.7 |
| 7,368,153 B2 | * | 5/2008 | Barmore et al. ............. 428/36.7 |
| 7,659,816 B2 | * | 2/2010 | Wandel .......................... 340/541 |
| 2003/0199095 A1 | * | 10/2003 | Yuyama et al. ................... 436/1 |
| 2004/0115819 A1 | * | 6/2004 | Puri ................................... 436/3 |
| 2007/0022095 A1 | | 1/2007 | Daos et al. |
| 2007/0212789 A1 | * | 9/2007 | Havens et al. ................ 436/138 |
| 2007/0220956 A1 | * | 9/2007 | Terentiev ....................... 73/49.2 |
| 2009/0123332 A1 | | 5/2009 | Whitehead et al. |

FOREIGN PATENT DOCUMENTS

| | | |
|---|---|---|
| FR | 2 822 445 A1 | 9/2002 |
| GB | 2056950 A | 3/1981 |
| WO | 96/12659 A1 | 5/1996 |
| WO | 00/04131 A1 | 1/2000 |
| WO | 01/04624 A1 | 1/2001 |

* cited by examiner

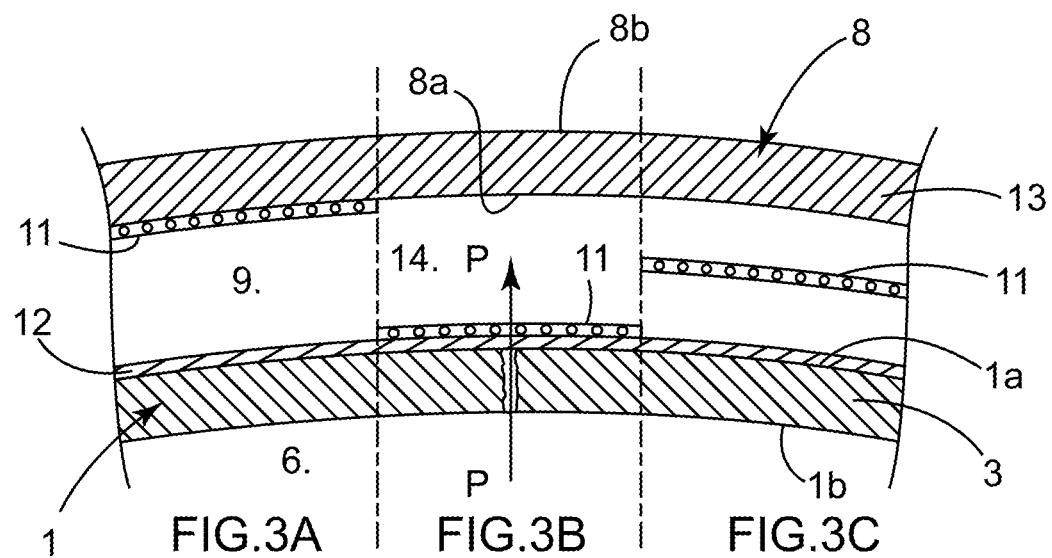
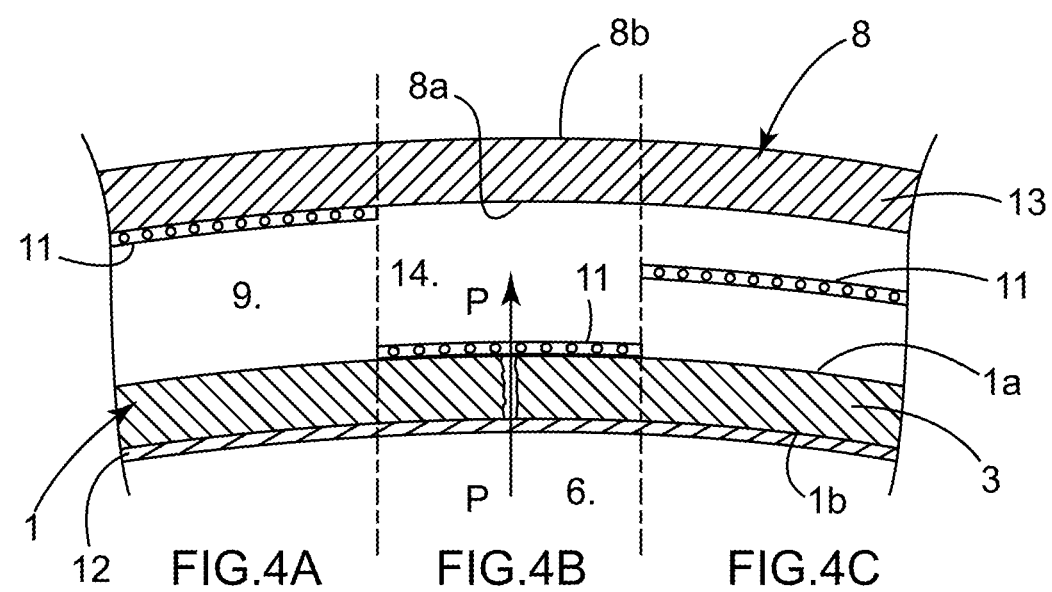

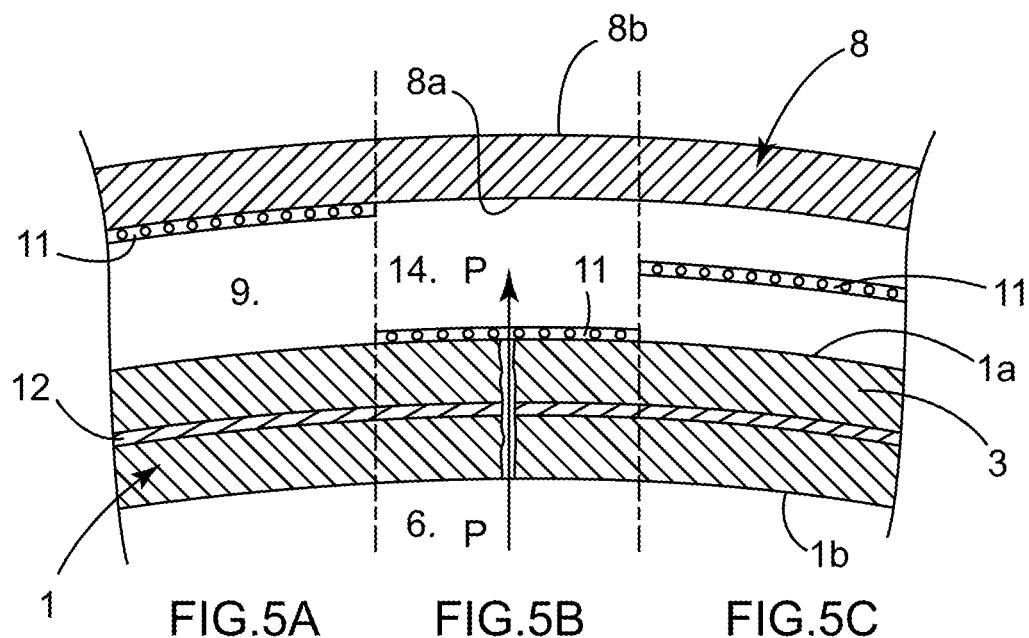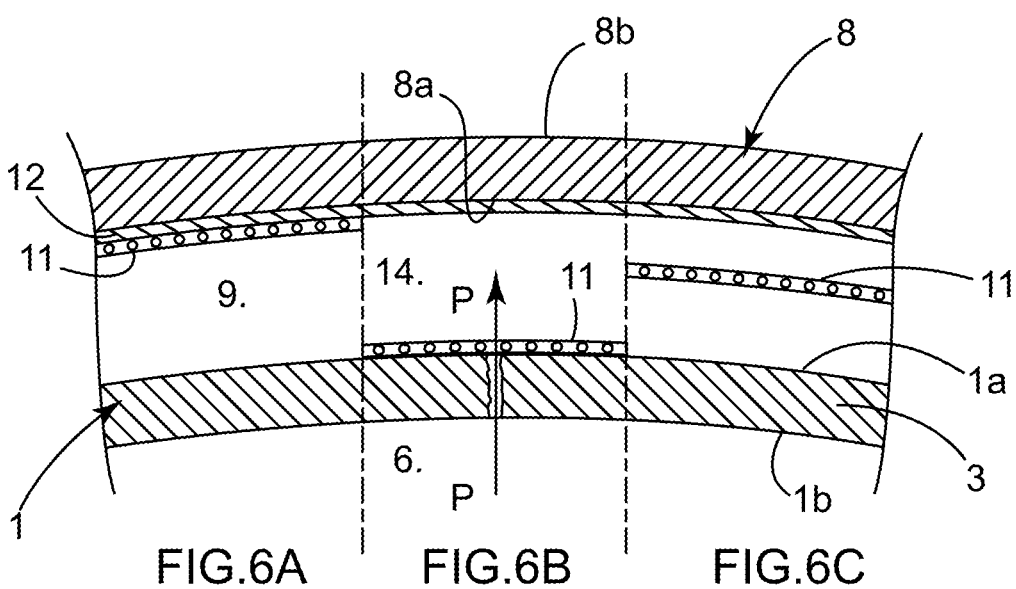

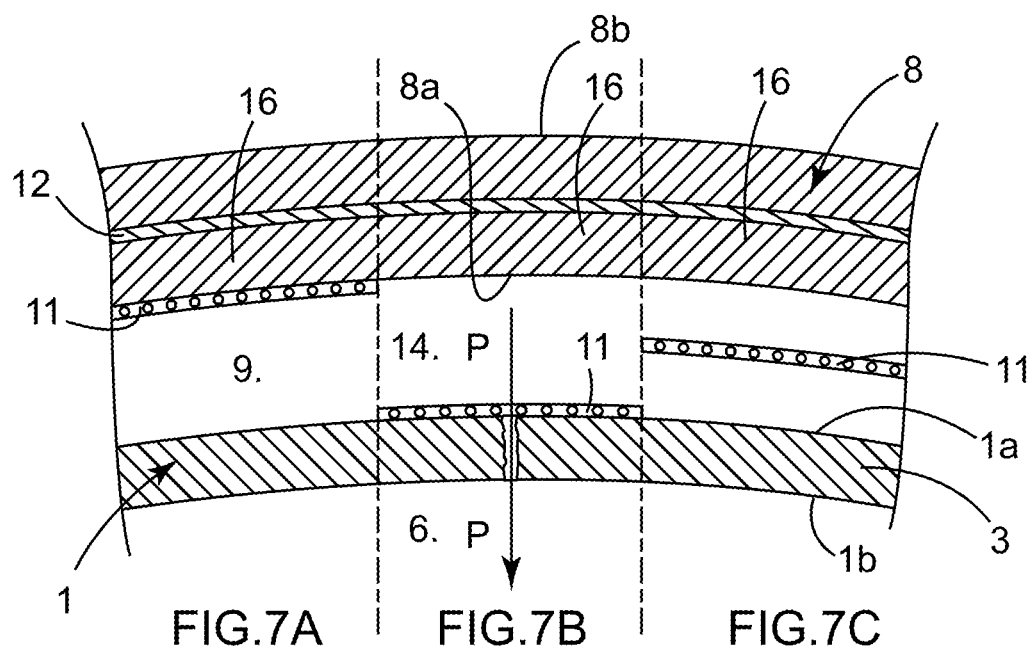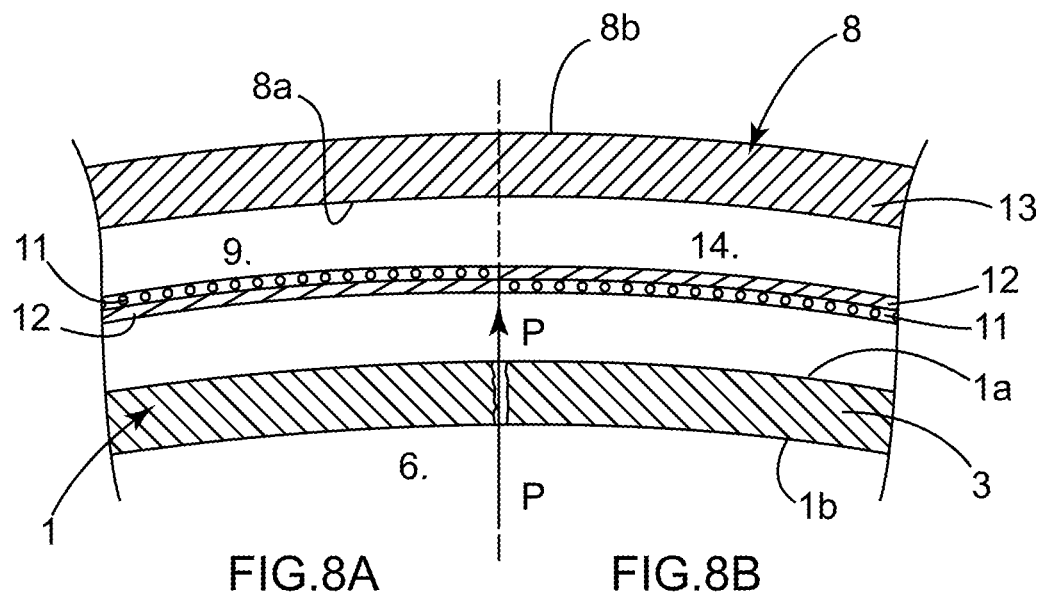

DETECTION OF THE INTEGRITY OF A TIGHT, CLOSED, SOFT PLASTIC POUCH FOR RECEIVING AND PROTECTING A PRODUCT OR A BIOPHARMACEUTICAL DEVICE

FIELD OF THE INVENTION

The invention relates to detecting the integrity of a fluid-tight, closed, flexible plastic pouch intended for receiving and protecting a biopharmaceutical product or device, such as a sterile pouch.

More specifically, the invention relates to an integrity/non-integrity indicator pouch, such a pouch when it is of satisfactory integrity, a method of producing such an integrity/non-integrity indicator pouch, a method of obtaining the actual pouch stricto sensu itself so that it is of satisfactory integrity, and lastly, a process for making use of a pouch stricto sensu which, when of satisfactory integrity, is intended to receive and protect a biopharmaceutical product or device.

BACKGROUND OF THE INVENTION

"Biopharmaceutical product" is understood to mean a product obtained from biotechnology—culture media, cell cultures, buffer solutions, artificial nutrition liquids, or a pharmaceutical product or more generally a product intended for use in the medical field. "Biopharmaceutical device" is understood to mean a device intended to be used in a process in the biological or pharmaceutical field—measurement or control means, means for processing a biopharmaceutical product, containers or parts of containers, transfer or closure means. Such biopharmaceutical products or devices are of high added value and it is important to be certain of their integrity, particularly the absence of contamination.

For the purposes of storage, shipment, or the execution of a process of a physical, chemical or biological nature, it is conventional to place such biopharmaceutical products or devices in disposable pouches that are flexible, closed, fluid-tight, sterile, and of plastic material such as polyethylene or a complex that includes polyethylene. Such a pouch comprises means for introducing into its inside space and means for removing from its inside space the biopharmaceutical product or device, it being possible to bring these means to their open or closed state according to the moment and the requirements.

There are known pouches of this type in which the two main walls are directly joined to each other. Once expanded, such pouches have a limited volume and remain relatively thin, which is why they are often called "pillow" or "2D" pouches (D meaning dimensions). Also known are 3D pouches which have two main walls connected by and sealed to two side gussets which can be folded flat or unfolded and spread open; the volume can then be at least 50 liters, and up to 3,000 liters or more. Such 3D pouches are described in document WO00/04131 or sold under the brand FLEXEL® 3D.

To be able to receive and protect a biopharmaceutical product or device as defined above effectively, it is essential that the inside space of the pouch—herein referred to as the pouch stricto sensu—and its contents, if any, are preserved from any deterioration originating from outside the pouch stricto sensu, such as contamination. This quality is referred to herein as "fluid-tightness". The pouch stricto sensu must therefore be fluid-tight or must at least present a degree of fluid-tightness considered to be satisfactory. Such a pouch stricto sensu is therefore designed and manufactured to have the required fluid-tightness. However, manufacturing defects in the pouch stricto sensu which affect its fluid-tightness cannot be ruled out. It is also possible for the fluid-tightness of an initially satisfactory pouch stricto sensu to be impacted after its production.

The fluid-tightness of the pouch stricto sensu is impacted once the pouch stricto sensu contains one or more passages through the envelope that it forms, including porousness, this or these passages having one or multiple outlets on the outer face of the pouch stricto sensu, including the welds between the component parts of the pouch stricto sensu in question.

Before using or considering the use of a pouch stricto sensu, it is therefore indispensable to be able to ensure that it has the required fluid-tightness. A pouch stricto sensu that has this fluid-tightness is said to be of satisfactory integrity and is suitable for receiving and protecting a biopharmaceutical product or device. A pouch stricto sensu that does not have this fluid-tightness is said to be of unsatisfactory integrity and, as it is unsuitable for receiving and protecting a biopharmaceutical product or device, must be set aside and not used.

Methods and devices are known for verifying the integrity of all pouches during production. Thus the ASTM International standard F 2095-01 which is entitled "Standard Test Methods for Pressure Decay Leak Test for Nonporous Flexible Packages With and Without Restraining Plates" more specifically concerns the pressure decay method. This method is considered in two modes of execution: with or without expansion restraining plates (for example the device known under the brand SARTOCHECK® 4). In all cases, such devices are complex and bulky, and are difficult to transport or use at the final location where the pouches are used.

Also, assuming the pouch is of satisfactory integrity when produced, an accidental loss or failure of integrity can occur after production and before final use of the pouch, for example during the storage, shipment, distribution, or delivery phases, or during the phase immediately preceding the use of the pouch. This risk is even greater for phases that are long (for example the storage phase may last several years) or that involve manipulating the pouch or placing it in contact with objects that could damage it. Such non-integrity cannot be detected by an integrity verification method performed at the pouch's point of manufacture, before the loss of integrity occurs.

Documents U.S. Pat. No. 6,892,567 and U.S. Pat. No. 6,196,056 describe methods and devices for determining the integrity of a package or compartment, based on sending a test gas through the package or the wall of the compartment. This device and the associated measurement instruments form a complex and bulky system.

Document US 2007/0220956 describes a method and device for detecting a leak in a bag intended for bioprocessing and containing a conductive fluid, placed in a rigid outer container, consisting of an electrically operated leak detector. Such a method and device have the same limits as mentioned above, except they only have applications in the case of a pouch filled with an electrically conductive fluid and the presence of a rigid outer container.

Document U.S. Pat. No. 4,098,577 describes a method and indicator for detecting the loss of integrity of a transparent package containing a product which is sealed when packaged. The package is filled with an artificial atmosphere such as carbon dioxide or nitrogen. A pH sensitive detector is placed in the package and is visible through it. The detector changes color if there is a loss of artificial atmosphere after a loss of integrity of the package. In the embodiments presented, the package is rigid, the product is a solid object, and the detector is kept separate from the product. This method is unsuitable for packaging intended to receive a fluid product that will be into contact with the detector. In addition, it does not describe or suggest that the detection occurs before the product is placed in the packaging, quite the opposite.

Document U.S. Pat. No. 4,813,541 describes a tamper-proof package and method. The package comprises a first internal container, rigid and hermetically sealed, filled with a first atmosphere and containing a substance, and a second external container, rigid and hermetically sealed, in which is located—kept apart by spacers—the first container, the inner cavity of the second container external to the first container being filled with a second atmosphere at a different pressure from that of the first atmosphere, and detection means placed in the cavity and sensitive to a change in the second atmosphere due to a loss of integrity of the first container or second container. Document U.S. Pat. No. 4,813,541, which describes a very specific structure, does not suggest having the detection occur before the substance is placed in the first container.

Document WO 01/04624 describes a colorimetric system comprising a detector sensitive to carbon dioxide.

Document WO96/12659 describes a so-called tamper-proof packaging that comprises an inner membrane delimiting an inner compartment which contains a first medium consisting of air, as well as an outer membrane delimiting an outer compartment which surrounds the inner compartment and contains a second medium consisting of carbon dioxide. An indicator tab, sensitive to the surrounding medium, is provided inside the outer compartment, and it can give an indication of a change in the first medium and in the second media.

Document U.S. Pat. No. 4,434,893 describes a package for receiving products comprising inner and outer containers. In one embodiment, the inner container and outer container have only one flexible wall, and these inner and outer containers are pressurized using a gas above atmospheric pressure in order to inflate their flexible walls. In another embodiment, the two walls of the inner and outer containers are flexible. The products—capsules, gelcaps, or the like—to be protected are inside the inner container, and the inner container is positioned at of the outer container so as to form a protection that prevents access to the products.

Document U.S. Pat. No. 4,436,203 describes a package comprising an inner enclosure of predefined size, loaded with a product and pressurized before being placed inside an outer enclosure. After its internal pressure is reduced to below the atmospheric pressure, said outer enclosure is closed. Thus, when one of the walls of the package is pierced, the consumer is alerted of the fact that the product may have been affected.

Document FR 2252 619 describes a device intended for use with a package that is normally closed with a hermetic seal. It comprises a detector arranged so that it is in communication with the interior of the package but is also visible from the outside. This detector contains a pH sensitive dye which has a first color at the normal atmospheric pH and a second color at a pH slightly greater than or less than the normal atmospheric pH.

Document FR-A-2822445 concerns a package for infectious samples, comprising a bag of fluid-tight plastic material intended to enclose a container containing said sample within a layer of absorbent cloth characterized by said fabric being dyed such that any trace of humidity modifies its initial color, the bag of plastic material being transparent.

Document U.S. Pat. No. 5,219,524 concerns a system for preserving an acid-containing article which is in contact with an alkaline substrate material and an artificial atmosphere which is substantially free of gaseous oxygen. The article, alkaline substrate material, and artificial atmosphere are hermetically sealed within a container, at least a portion of the container being at least partially transparent so as to permit viewing the article from outside the container.

The invention therefore has the aim of overcoming the problems mentioned above, and permitting the determination of the integrity or non-integrity of a pouch stricto sensu at any desired moment after its manufacture and at least immediately prior to its planned use, in a certain, easy, and rapid manner, without requiring a bulky or complex dedicated device, or difficult or delicate operations, and without requiring specialized personnel specially and exclusively dedicated to integrity verification, and without needing to perform positive testing on the pouch to ensure its integrity, its non-integrity being indicated automatically and therefore without requiring positive testing of each pouch when the pouch is one of a plurality of pouches.

To this effect, a first aspect of the invention relates to an integrity/non-integrity indicator pouch, intended for receiving and protecting a biopharmaceutical product or device, comprising:

a first, inner, envelope which is flexible, closed, fluid-tight, and of plastic material, comprising a wall delimiting a first space, forming a pouch stricto sensu intended to receive the biopharmaceutical product or device, comprising first introduction means and first extraction means for respectively introducing/extracting the product or device, said means being in the closed state, a second, outer, envelope which is closed, fluid-tight, and of plastic material, comprising a wall delimiting a second space in which is located the first envelope/pouch stricto sensu, comprising second introduction means and second extraction means for respectively introducing/extracting the first envelope/pouch stricto sensu, said means being in the closed state, an intermediate space thus being arranged in the second space outside the first envelope/pouch stricto sensu, spacing means placed between the wall and the wall, such that the inner face of the wall does not occlude any integrity-impacting opening on the outer face of the wall, at least one tracer gas, located either in the first space or in the intermediate space, at a partial pressure that is different from that of the intermediate space or of the first space, respectively, introduced into the first space and/or the intermediate space by tracer gas introduction means, now in the closed state, at least one continuous colorimetric detection layer for detecting the tracer gas, responding to the concentration of the tracer gas which reaches it by changing from a first color to a second and different color, being an integral part of a wall of the first envelope/pouch stricto sensu and/or of a wall of the second envelope and/or of the spacer means, the arrangement of the walls of the first envelope/pouch stricto sensu and of the second envelope, the spacer means, the tracer gas, and the colorimetric detection layer, on the one hand, and the permeability or impermeability to the tracer gas of the colorimetric detection layer, and of the spacer means, on the other hand, being chosen so that the colorimetric detection layer cannot be reached by tracer gas located in the intermediate space or in the first space at a concentration beyond the transition value, when the first envelope/pouch stricto sensu is of satisfactory integrity, and so that the colorimetric detection layer is in any case reached by the tracer gas located in the intermediate space or in the first space at a concentration beyond the transition value, when the first envelope/pouch stricto sensu is of unsatisfactory integrity.

Thus, if the colorimetric detection layer is identified as being of the first color, the first envelope/pouch stricto sensu is considered to be of satisfactory integrity and suitable for receiving and protecting the biopharmaceutical product or device, but if it is identified as being of the second color, it is considered to be of unsatisfactory integrity and unsuitable for receiving and protecting the biopharmaceutical product or device.

In some embodiments, the spacer means comprise at least one porous layer fully and functionally covering the outer face of the wall of the first envelope/pouch stricto sensu and/or the inner face of the wall of the second envelope and/or the face of the colorimetric detection layer facing the intermediate space; or the spacer means comprise at least one porous layer which either structurally covers the outer face of the wall of the first envelope/pouch stricto sensu and/or the inner face of the wall of the second envelope and/or the face of the colorimetric detection layer facing the intermediate space, or is placed within the intermediate space.

In some embodiments, either the tracer gas is in the first space at a higher partial pressure than in the intermediate space, and the colorimetric detection layer changes from the first color to the second color in response to the concentration of tracer gas which reaches it rising above a transition value, or the tracer gas is in the first space at a lower partial pressure than in the intermediate space, and the colorimetric detection layer changes from the first color to the second color in response to the concentration of tracer gas which reaches it falling below a transition value.

In a first family of embodiments, a colorimetric detection layer is permeable to the tracer gas and is an integral part of the wall of the first envelope/pouch stricto sensu, being located on the outer face and in the intermediate space, or located on the inner face and in the first space, or inserted within the wall, between its outer face and its inner face and between the first space and the intermediate space.

In a second family of embodiments, a colorimetric detection layer is an integral part of the wall of the second envelope, being either located on the inner face and in the intermediate space, or inserted within the wall, between the inner face and its outer face, the layer of the wall of the second envelope adjacent on one side to the colorimetric detection layer and on the other side to the inner face then being permeable to the tracer gas.

In a third family of embodiments, a colorimetric detection layer is an integral part of a porous layer of the spacer means which is either located near the outer face of the wall of the first envelope/pouch stricto sensu or is located near the inner face of the second envelope, or a colorimetric detection layer and a porous layer of the spacer means are structurally combined to form a single layer.

Where applicable, the embodiments of these different families may be combined.

Depending on the case, the first envelope/pouch stricto sensu is a 2D pouch, or a 3D pouch comprising two gussets. In the latter case, and according to one embodiment, the spacer means comprise at least one porous layer which fully and functionally, and structurally where necessary, covers the outer face of the interior of the gussets.

In some possible embodiments, the spacer means comprise at least one porous layer which fully and functionally, and structurally where necessary, covers the first introduction means and the first extraction means for respectively introducing/extracting the biopharmaceutical product or device and the tracer gas introduction means of the first envelope/pouch stricto sensu. Or, the spacer means comprise at least one porous layer of fabric, nonwoven fabric, PE, PP, PTFE.

In some possible embodiments, a tracer gas is chosen from among the group comprising oxygen, carbon dioxide, and helium.

In two possible embodiments, one among the first space or the intermediate space contains tracer gas and the other among the intermediate space or the first space does not contain or substantially does not contain tracer gas.

In one embodiment, the second envelope allows identifying from outside of itself whether the colorimetric detection layer is of the first color or the second color.

In one embodiment, the second envelope is flexible.

In one embodiment, the integrity/non-integrity indicator pouch additionally comprises an outer protective packaging which houses the second envelope within which the first envelope/pouch stricto sensu is located.

A second aspect of the invention relates to an integrity/non-integrity indicator pouch of satisfactory integrity, consisting of an integrity/non-integrity indicator pouch as described above where the colorimetric detection layer is of the first color.

A third aspect of the invention relates to a method for creating an integrity/non-integrity indicator pouch as described above, wherein:
  one provides a first envelope/pouch stricto sensu, a second envelope in which the second introduction means for introducing the first envelope/pouch stricto sensu are in the open state, spacer means, the tracer gas, the colorimetric detection layer which is an integral part of a wall of the first envelope/pouch stricto sensu and/or of a wall of the second envelope and/or of the spacer means,
  the first envelope/pouch stricto sensu is introduced into the second space of the second envelope via the second introduction means in the open state, the spacer means being placed between the wall and the wall such that the inner face of the wall does not occlude any integrity-impacting opening in the outer face of the wall,
  the tracer gas is introduced into either the first space or the intermediate space, at a partial pressure that is different from that of the intermediate space or of the first space, respectively, via the tracer gas introduction means which are in the open state, then these introduction means are brought to the closed state,
  the arrangement is chosen so that the colorimetric detection layer cannot be reached or conversely is necessarily reached by the tracer gas, as required, and the permeability or impermeability to the tracer gas of the colorimetric detection layer and of the spacer means is accordingly chosen so that the colorimetric detection layer is in fact reached by the tracer gas when such is necessary,
  the first envelope/pouch stricto sensu and the second envelope being closed.

A fourth aspect of the invention relates to a method for obtaining a pouch stricto sensu of satisfactory integrity and ready to receive and protect a biopharmaceutical product or device, wherein:
  one provides an integrity/non-integrity indicator pouch as described above,
  the colorimetric detection layer is identified as being of the first color or the second color,
  if the colorimetric detection layer is of the first color:
    the second extraction means, with which the second envelope is equipped in order to extract the first envelope/pouch stricto sensu, are brought to the open state, the first envelope/pouch stricto sensu is extracted from the second space of the second envelope, and the first introduction means, with which the first envelope/pouch stricto sensu, considered to be of satisfactory integrity, is equipped in order to introduce the biopharmaceutical product or device, are brought to the open state in order to place the biopharmaceutical product or device within, whereas if the colorimetric detection layer is of the second color, the first envelope/pouch stricto sensu is considered to be of unsatisfactory integrity and is not used for placing a biopharmaceutical product or device within.

A fifth aspect of the invention relates to a process for making use of a pouch stricto sensu, which when of satisfactory integrity is intended for receiving and protecting a biopharmaceutical product or device, said process comprising:

at a point of manufacture, initial operations consisting of manufacturing a pouch stricto sensu, at a point of use, final operations consisting of using the pouch stricto sensu by placing the biopharmaceutical product or device within, intermediate storage, shipping, and handling operations, at one or more locations, and comprising:

the creation by the method described above, at the point of manufacture, of an integrity/non-integrity indicator pouch comprising a first envelope/pouch stricto sensu, the shipping of the integrity/non-integrity indicator pouch from the point of manufacture to the point of use, including storage and handling operations when there are such, and, at least at the point of use and before extracting the first envelope/pouch stricto sensu from the second envelope in order to place the biopharmaceutical product or device within, the identification of whether the colorimetric detection layer is of the first color or the second color, if the colorimetric detection layer is identified as being of the first color, the first envelope/pouch stricto sensu is considered to be of satisfactory integrity and is used for placing the biopharmaceutical product or device within in order to receive and protect it, whereas if the colorimetric detection layer is identified as being of the second color, the first envelope/pouch stricto sensu is considered to be of unsatisfactory integrity and is not used for placing the biopharmaceutical product or device within.

In one embodiment, the identification of whether the colorimetric detection layer is of the first color or the second color is done concurrently with the intermediate storage, shipping, or handling operations.

In one embodiment, the identification of whether the colorimetric detection layer is of the first color or the second color is done at the point of use immediately prior to extracting first envelope/pouch stricto sensu from the second envelope in order to place the biopharmaceutical product or device within.

BRIEF DESCRIPTION OF THE DRAWINGS

Several embodiments of the invention are now described with reference to the attached drawings, in which:

FIGS. 3A, 3B and 3C are three partial transverse cross-sectional views at a larger scale, illustrating three possible embodiments of the integrity/non-integrity indicator pouch, in which the colorimetric detection layer is located next to the outer face of the wall of the first envelope/pouch stricto sensu of which it is an integral part, the spacing means being respectively associated with the inner face of the wall of the second envelope (FIG. 3A), associated with the wall of the first envelope/pouch stricto sensu next to its outer face (FIG. 3B), or located between the walls of the first envelope/pouch stricto sensu and of the second envelope (FIG. 3C).

FIGS. 4A, 4B and 4C are three transverse partial cross-sectional views at a larger scale, illustrating three possible embodiments of the integrity/non-integrity indicator pouch, in which the colorimetric detection layer is located next to the inner face of the wall of the first envelope/pouch stricto sensu of which it is an integral part, the spacer means being respectively associated with the inner face of the wall of the second envelope (FIG. 4A), associated with the outer face of the wall of the first envelope/pouch stricto sensu (FIG. 4B), or located between the walls of the first envelope/pouch stricto sensu and of the second envelope (FIG. 4C).

FIGS. 5A, 5B and 5C are three partial transverse cross-sectional views at a larger scale, illustrating three possible embodiments of the integrity/non-integrity indicator pouch, in which the colorimetric detection layer is inserted into the wall of the first envelope/pouch stricto sensu of which it is an integral part, the spacing means being respectively associated with the inner face of the wall of the second envelope (FIG. 5A), associated with the outer face of the wall of the first envelope/pouch stricto sensu (FIG. 5B), or located between the walls of the first envelope/pouch stricto sensu and of the second envelope (FIG. 5C).

FIGS. 6A, 6B and 6C are three partial transverse cross-sectional views at a larger scale, illustrating three possible embodiments of the integrity/non-integrity indicator pouch, in which the colorimetric detection layer is located next to the inner face of the wall of the second envelope of which it is an integral part, the spacer means being respectively associated with the wall of the second envelope next to its inner face (FIG. 6A), associated with the outer face of the wall of the first envelope/pouch stricto sensu (FIG. 6B), or located between the walls of the first envelope/pouch stricto sensu and of the second envelope (FIG. 6C).

FIGS. 7A, 7B and 7C are three transverse partial cross-sectional views at a larger scale, illustrating three possible embodiments of the integrity/non-integrity indicator pouch, in which the colorimetric detection layer is inserted into the wall of the second envelope of which it is an integral part, the spacer means being respectively associated with the inner face of the wall of the second envelope (FIG. 7A), associated with the outer face of the wall of the first envelope/pouch stricto sensu (FIG. 7B), or located between the walls of the first envelope/pouch stricto sensu and of the second envelope (FIG. 7C).

FIGS. 8A and 8B are two transverse partial cross-sectional view at a larger scale, illustrating three possible embodiments of the integrity/non-integrity indicator pouch, in which the colorimetric detection layer is an integral part of a porous layer of the spacer means, the colorimetric detection layer being located near the outer face of the first envelope/pouch stricto sensu wall (FIG. 8A), or located near the inner face of the second envelope (FIG. 8B).

DESCRIPTION OF THE PREFERRED EMBODIMENTS

Figure 1:
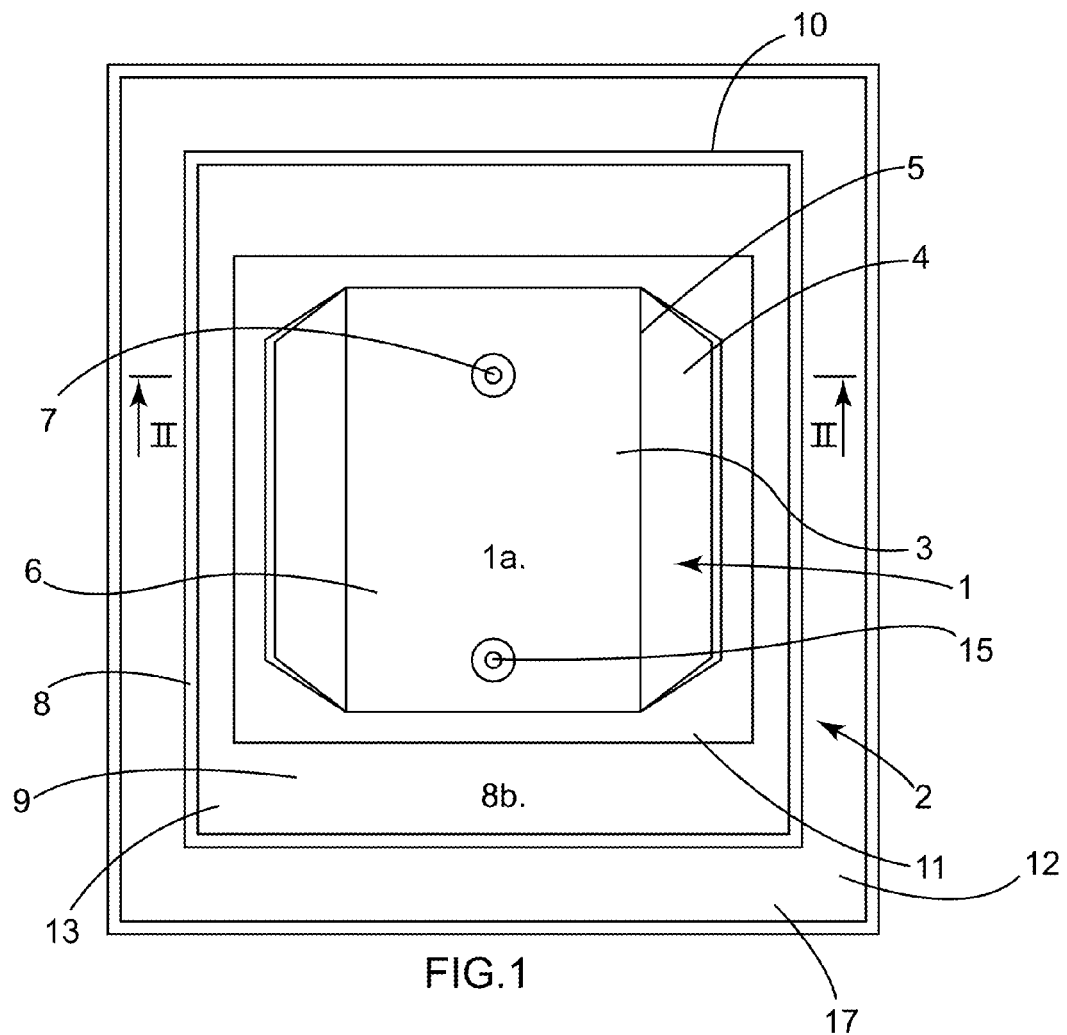
FIG. 1 is a top view of an integrity/non-integrity indicator pouch, of the type in which the pouch stricto sensu is a 3D pouch and the integrity/non-integrity indicator pouch is contained within an outer protective packaging, this pouch represented as folded flat for storage or shipment for example.
Figure 2:
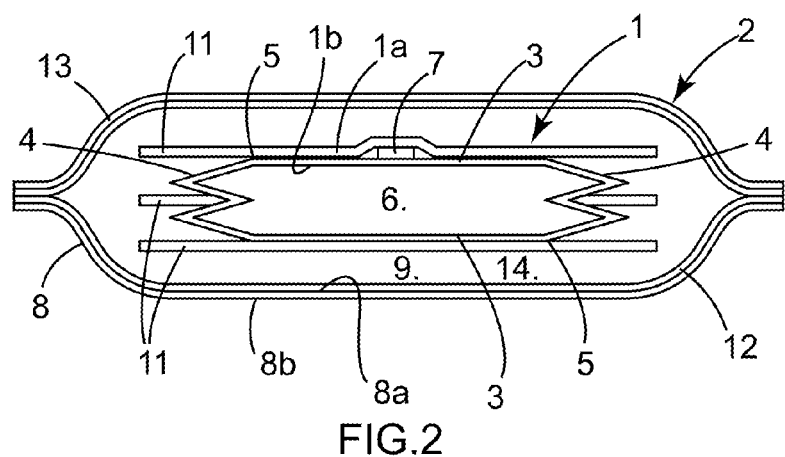
FIG. 2 is a transverse cross-sectional view of the integrity/non-integrity indicator pouch of FIG. 1, without the outer protective packaging, in one possible and non-limiting embodiment.

A flexible 3D pouch 1 that is closed (during the phases where such is desired), fluid-tight as a whole, sterile, of plastic material, and in particular for one-time use, intended in the biopharmaceutical field for receiving and protecting during storage of, shipment of, or when performing a process that is physical, chemical, or biological in nature on, a biopharmaceutical product or a device, is known from the prior art (see for example document WO00/04131 and the pouch known under the brand FLEXEL® 3D).

To be able to receive and protect the biopharmaceutical product or device effectively, the space inside the pouch 1 and its possible contents must be protected from possible deterioration originating from outside the pouch 1, such as contamination. The pouch 1 must therefore be fluid-tight in the defined sense. Such a pouch 1 is designed and manufactured to be fluid-tight, but manufacturing defects cannot be ruled out and the fluid-tightness may be impacted after manufacture.

The fluid-tightness is impacted when the pouch 1 has one or more passages T through the envelope that it forms, including porousness, this or these passages having one or more outlets D on the outer face 1a of the pouch 1, including the welds 5 between the component parts of the pouch 1 in question.

Before using or considering the use of such a pouch 1, it is therefore essential to ensure that it provides the fluid-tightness required. When the pouch 1 is "of satisfactory integrity", it is able to receive and protect a biopharmaceutical product or device, while a pouch 1 not providing such fluid-tightness is said to be "of unsatisfactory integrity" and, being unsuitable for receiving and protecting a biopharmaceutical product or device, must be set aside and not used in a process that makes use of the pouches 1.

The invention aims to identify the integrity or non-integrity of such a pouch 1 at any desired moment after its manufacture, and at least immediately prior to its planned use.

To do this, a pouch 2 is utilized which receives the pouch 1.

To distinguish between the pouches 1 and 2, pouch 1 is referred to as the "pouch stricto sensu" while pouch 2 is referred to as the "integrity/non-integrity indicator pouch".

The expression "pouch stricto sensu" therefore concerns to the pouch 1 that directly receives and protects the biopharmaceutical product or device. This pouch stricto sensu 1 is incorporated into the assembly of the invention referred to as the "integrity/non-integrity indicator pouch" 2.

A 3D pouch stricto sensu 1 can be of significant volume, of at least 50 liters and up to 1,000 liters or more. Such a pouch stricto sensu 1 typically comprises a main wall 3 of two parts connected by welds 5 in a fixed and fluid-tight manner to two lateral gussets 4.

Such a 3D pouch stricto sensu can be folded flat—for example for storage, shipping, or handling—or unfolded and spread out, when it receives a biopharmaceutical product or device.

The fluid-tight component walls 3, 4 and the welds 5 of the pouch 1 form an envelope, referred to herein as the "first envelope", also denoted by the reference 1. "The wall" 3, 4 is used to refer to the set of walls of the pouch stricto sensu 1 as well as to each of the walls.

The wall 3, 4 is made of one of more flexible plastic materials, at least some of them being non-porous so that the pouch stricto sensu 1 is fluid-tight as a whole. The wall 3, 4 may be a single layer or multiple layers. It may incorporate a high-gas-barrier plastic, such as EVOH, although this is a non-limiting example.

The pouch stricto sensu 1, meaning its wall 3, 4, comprises an outer face 1a and an inner face 1b. The terms "outer" and "inner" are respectively understood to be relative to what is outside and inside the pouch stricto sensu 1. The interior of the pouch stricto sensu 1 delimits a first space 6, its boundary being the inner face 1b and its volume being appropriate for receiving the biopharmaceutical product or device when such is desired to be placed within the pouch stricto sensu 1.

The pouch stricto sensu 1 comprises first introduction means 7 associated with the wall 3, for introducing the biopharmaceutical product or device into the first space 6 when such is desired. This occurs after the pouch stricto sensu 1 has been extracted from the integrity/non-integrity indicator pouch 2. Such first introduction means 7 may be in the form of one or more passages arranged within the wall 3, in order to be brought to, or to be in, the open state when necessary. Such passages are generally arranged so that they can then be brought to the closed state, in particular by welding, once the biopharmaceutical product or device is introduced into the first space 6.

The pouch stricto sensu 1 also comprises first extraction means associated with the wall 3, for extracting the biopharmaceutical product or device from the first space 6 when so desired. Such extraction can only occur if the pouch stricto sensu 1 has been previously extracted from the integrity/non-integrity indicator pouch 2 in order to introduce the biopharmaceutical product or device as just described. Such first extraction means may involve an irreversible tearing or a similar action of the wall 3 of the pouch stricto sensu 1, which is generally for one-time use.

Such a pouch stricto sensu 1 is typically in a flat folded state, for example for storage, shipping, or handling, or in an unfolded spread open state for receiving and protecting the biopharmaceutical product or device, or in an intermediate state. The pouch stricto sensu 1 can be reshaped to change from one to another of these states.

Such a pouch stricto sensu 1 can, depending on requirements, be associated with a rigid container which externally contains the pouch 1. For example, a container such as this is described in a possible variant embodiment in document EP-A-1012073, or available under the brand PALLETTANK®.

The process of making use of such a pouch stricto sensu 1 comprises:
- at a point of manufacture, initial operations consisting of manufacturing the pouch stricto sensu 1,
- at a point of use, usually different from and at a distance from the point of manufacture, final operations consisting of using the pouch stricto sensu 1 by placing the biopharmaceutical product or device within for the desired purpose,
- and at one or more locations (fixed or mobile), intermediate storage, shipping, handling, or other operations, which may extend over a fairly long period, several months for example, or even several years where storage is concerned.

In order to identify the integrity or non-integrity of the pouch stricto sensu 1 at any desired moment after its manufacture and at least immediately prior to its planned use, the process for making use of the pouches stricto sensu is modified in accordance with the invention.

This process first comprises the creation, at the point of manufacture, of an integrity indicator pouch 2 comprising the pouch stricto sensu 1.

We will now describe an integrity/non-integrity indicator pouch comprising a pouch stricto sensu 1 which is either a 3D pouch, as mentioned above, or a 2D pouch which has no gussets 4.

The integrity/non-integrity indicator pouch 2 firstly comprises the pouch stricto sensu 1, also referred to as the "first envelope" 1.

Within the integrity/non-integrity indicator pouch 2, the first envelope/pouch stricto sensu 1 is closed and empty of biopharmaceutical product or device. Its first introduction means 7 and its first extraction means are in the closed state.

The integrity/non-integrity indicator pouch 2 next comprises a second, external, envelope 8, the first envelope/pouch stricto sensu 1 being internal and intended to be placed within the second envelope 8.

The second envelope 8 comprises a wall 13 which most often has several parts welded together at fluid-tight welds. "The wall" 13 is understood to refer to a single wall 13 as well as to all of these wall parts or to each of them if there are more than one.

The second envelope 8 is closed and fluid-tight. It is preferably flexible, so that it can lie flat during storage, shipping, and handling.

The wall 13 is made or one of more plastic materials, flexible if the second envelope 8 is flexible, and non-porous so that the second envelope 8 is fluid-tight as a whole. The wall 13 may be of a single layer or multiple layers. It may incorporate a high-gas-barrier plastic, such as EVOH, although this is a non-limiting example.

The second envelope 8, meaning its wall 13, comprises an inner face 8a and an outer face 8b. The terms "inner" and "outer" are respectively understood as being in relation to what is located at the inside and outside of the second envelope 8. The interior of the second envelope 8 delimits a second space 9, its boundary being the inner face 8a and its volume appropriate for receiving the pouch 1 stricto sensu, here empty of biopharmaceutical product or device.

The second envelope 8 comprises second introduction means 10 associated with the wall 13, for the purpose of prior introduction, when this is desired, of the first envelope/pouch stricto sensu 1 into the second space 9. Such an introduction occurs for and during the creation of the integrity/non-integrity indicator pouch 2. Such second introduction means 10 can be in the form of one or more passages arranged in the wall 13 which can be brought to or be in the open state and then be brought to the closed state, in particular by welding, once the first envelope/pouch stricto sensu 1 is introduced into the second space 9.

The second envelope 8 also comprises second extraction means associated with the wall 13, for the purpose of the extraction, when this is desired, of the first envelope/pouch stricto sensu 1 from the second space 9. Such extraction occurs at the time of, and before, the introduction of the biopharmaceutical product or device into the first space 6. Such second extraction means may involve an irreversible tearing or similar action of the wall 13 of the second envelope 8, which is generally for one-time use.

In the integrity/non-integrity indicator pouch 2, the first envelope/pouch stricto sensu 1 is located within the second space 9 of the second envelope 8, with the second introduction means 10 and the second extraction means here being in the closed state.

Outside the first envelope/pouch stricto sensu 1 but inside the second envelope 8, a space 14 is formed that is referred to as the "intermediate space", located inside the second space 9 and outside the first envelope/pouch stricto sensu 1. The boundaries of the intermediate space 14 are the outer face 1a of the first envelope/pouch stricto sensu 1 and the inner face 8a of the second envelope 8.

The integrity/non-integrity indicator pouch 2 then comprises spacer means 11, housed within the space 14 and placed between the wall 3, 4 of the first envelope/pouch stricto sensu 1 and the wall 13 of the second envelope 8. These spacer means 11 are such that the inner face 8a of the wall 13 of the second envelope 8 does not occlude any integrity-impacting opening D in the outer face 1a of the wall 3, 4 of the first envelope/pouch stricto sensu 1.

The spacer means 11 comprise one or more porous layers completely and functionally covering the outer face 1a of the wall 3, 4 of the first envelope/pouch stricto sensu 1 and/or the inner face 8a of the wall 13 of the second envelope 8 and/or the face of a colorimetric detection layer 12 facing the intermediate space 14, which will be further discussed below.

A layer of the spacer means 11 is porous due to either an arrangement that achieves porousness or by the use of one or more porous materials. For example, the spacer means 11 comprise one or more porous layers of fabric, nonwoven fabric, PE, PP, PTFE, or other similar material.

"Porousness" is understood here to mean that the spacer means 11 comprise a multiplicity of interstitial spaces adjacent to each other, traversing the layer(s) constituting the spacer means 11 from one side to the other, such that any integrity-impacting opening D if there is such in the outer face 1a of the wall 3, 4 of the first envelope/pouch stricto sensu 1 must necessarily be facing and in communication with at least one interstitial outlet and that a gas, such as a tracer gas which will be further discussed below, can traverse the spacer means from one side to the other.

"Completely functionally covering" is understood here to mean that the spacer means 11 extend over the entire surface of the outer face 1a, of the inner face 8a, or of the face of the colorimetric detection layer 12 facing the intermediate space 14, even if the spacer means 11 are not in contact with the face in question, provided that any possible integrity-impacting opening D on the face in question is prevented from being occluded due to the spacer means 11.

Four embodiments are envisaged for the arrangement of the structure of the spacer means 11 in layer form relative to the first envelope/pouch stricto sensu 1 and to the second envelope 8. Where necessary, these four embodiments can be combined.

In a first embodiment (FIGS. 3B, 4B, 5B, 6B, 7B), the spacer means 11 in layer form structurally cover the outer face 1a of the wall 3, 4 of the first envelope/pouch stricto sensu 1.

In a second embodiment (FIGS. 3A, 4A, 5A, 7A), the spacer means 11 in layer form structurally cover the inner face 8a of the wall 13 of the second envelope 8.

In a third embodiment (FIGS. 3B, 6A), the spacer means 11 in layer form structurally cover the face of the colorimetric detection layer 12 facing the intermediate space 14.

In a fourth embodiment (FIGS. 3C, 4C, 5C, 6C, 7C, 8A, 8B), the spacer means 11 in layer form are placed in the intermediate space 14.

"Structurally cover" is understood here to mean that the spacer means 11 extend over and are in contact with the outer face 1a, the inner face 8a, the face of the colorimetric detection layer 12 facing the intermediate space 14, including when the spacer means 11 are structurally a part of a wall or layer 3, 4, 13 and 12 such that they are inseparable or nearly inseparable or in a similar manner.

In the case where the first envelope/pouch stricto sensu 1 is a 3D pouch, the spacer means in layer form 11 completely functionally cover, and structurally as well when necessary, the outer face of the inside of each of the two gussets 14. The "outer" face concerned here is understood to mean the outer face 1a. The "inside of a gusset" is understood to mean the portion of the gusset adjoining the inward fold. With a gusset 4, it would be possible in the absence of spacer means such as the spacer means 11, for the two outer faces of the two parts of the gusset 4 adjoining the inward fold to come into contact with one another and that a possible integrity-impacting opening D on one of the outer faces is then occluded by the other outer face. Because of the presence of the spacer means 11 in each gusset 14, there is no such risk because any such occlusion is prevented.

In one embodiment, the spacer means in layer form 11 completely functionally cover, and structurally where necessary, the first introduction means 7 and the first extraction means for the biopharmaceutical product or device, as well as the tracer gas introduction means 15 with which the first envelope/pouch stricto sensu 1 may possibly be equipped.

The spacer means 11 in layer form have a flexibility which allows them to follow the shape of the wall or layer 3, 4, 13 and 12, which is itself flexible.

The integrity/non-integrity indicator pouch 2 then comprises one or more chosen tracer gases and one or more colorimetric detectors 12 of this or these tracer gases, adapted for it or them.

The tracer gas is either in the first space 6 of the first envelope/pouch stricto sensu 1, or in the intermediate space 14 of the second envelope 8, at a partial pressure that is different from the partial pressure that it has in the intermediate space 14 or the first space 6, respectively. This definition also includes the case where one among the first space 6 or intermediate space 14 contains tracer gas and the other among the intermediate space 14 or first space 6 does not contain or substantially does not contain tracer gas, the partial pressure p being zero or near zero.

The tracer gas is introduced into the first space 6 of the first envelope/pouch stricto sensu 1 and/or into the intermediate space 14 of the second envelope 8 by tracer gas introduction means 15, respectively associated with the first envelope/pouch stricto sensu 1 and/or the second envelope, at the corresponding wall 3 and/or wall 13. Such tracer gas introduction means 15 may be a valve, a port, a closable opening, or a similar arrangement. The gas tracer introduction means 15 can be placed in the open state in order to introduce the tracer gas, or to discharge it if such is desired. They may also be placed in the closed state outside of these circumstances and particularly during storage and shipment of the integrity/non-integrity indicator pouch 2, when the process that results in identifying the integrity/non-integrity of the integrity/non-integrity indicator pouch 2 is carried out.

In the integrity/non-integrity indicator pouch 2, here the tracer gas introduction means 15 are in the closed state.

Such a tracer gas can be chosen from among the group comprising oxygen, carbon dioxide, and helium, although this list is only a non-limiting example.

A colorimetric detector 12 of tracer gas comprises one or more continuous layers for colorimetric detection of the tracer gas.

Such a continuous colorimetric detection layer 12 responds, meaning it is sensitive, to the concentration of tracer gas that reaches it by changing from a first color to a second color that is different from the first color, when the concentration of tracer gas reaching it goes beyond a certain transition value. Such a transition value is known, for each pairing of tracer gas/continuous colorimetric detection layer 12.

Such a colorimetric detection layer 12 has the constructive structural or functional characteristic of being an integral part of a wall 3, 4 of the first envelope/pouch stricto sensu 1 and/or of a wall 13 of the second envelope 8 and/or of the spacer means 11, depending on the planned configurations. This is understood to mean that the colorimetric detection layer 12 is not located within, meaning in the middle of the first space 6 or of the second space 9, except in the case where it is an integral part of the spacer means 11 which are themselves located within the intermediate space 14.

The colorimetric detection layer 12 has a flexibility enabling it to follow, to the extent necessary, the shape of the wall or layer 3, 4, 13 and 11, which is itself flexible.

Such a colorimetric detection layer 12 forms an autonomous colorimetric detector, without an internal energy source or external connections.

The first color and the second color which the colorimetric detection layer 12 can assume must be distinguishable from each other so that it is possible to identify unambiguously and without error whether the colorimetric detection layer 12 is of the first color or the second color. Such identification of the color can be done by a human (an outside observer) or can be more or less automated.

The integrity/non-integrity indicator pouch 2 comprising the spacer means 11, the tracer gas, and the colorimetric detection layer 12, can be flattened or substantially flattened onto itself and is therefore easily made suitable for storage, shipment, or handling.

In one embodiment (FIGS. 3A, 3B, 3C, 4A, 4B, 4C, 5A, 5B, 5C, 6A, 6B, 6C, 8A, 8B), the tracer gas is in the first space 6 at a partial pressure P that is greater than the partial pressure p in the intermediate space 14. In this case, the colorimetric detection layer 12 changes from the first color to the second color in response to the concentration of tracer gas that reaches it rising above the transition value.

In another embodiment (FIGS. 7A, 7B, 7C), the tracer gas is in the first space 6 at a partial pressure p that is smaller than the partial pressure P in the intermediate space 14. In this case, the colorimetric detection layer 12 changes from the first color to the second color in response to the concentration of tracer gas that reaches it falling below the transition value.

It is understood that the presence and the choice of tracer gas and the difference in pressure P-p thereof has no function other than to cause the color of the colorimetric detection layer 12 to change according to whether there is an integrity-impacting opening in the outer face 1a of the wall 3, 4. The amount and the pressure of the tracer gas do not need to be significant.

The integrity/non-integrity indicator pouch 2 comprising the two envelopes 1 and 8, the spacer means 11, the tracer gas, and the colorimetric detection layer 12, can be presented in its flat form for storage, shipment, and handling.

If the wall 3, 4 (including the welds 5) of the first envelope/pouch stricto sensu 1 is of satisfactory integrity, the tracer gas remains in the initial state in which it was introduced into the integrity/non-integrity indicator pouch 2, the difference in the initial pressure on each side of the first wall 3, 4 being maintained.

If the integrity of the wall 3, 4 is unsatisfactory, due to one or more passages T traversing the first envelope/pouch stricto sensu 1, with one or more outlets D on the outer face 1a, the difference in the initial pressure of the tracer gas decreases over time, possibly until it disappears, as the tracer gas traverses the first envelope/pouch stricto sensu 1 by traveling through the passage(s) T and the outlet(s) D, in the direction heading from the chamber where the partial pressure is highest to the chamber where the partial pressure is lowest. The partial pressure of the tracer gas in the chamber where it has the highest partial pressure decreases, and the partial pressure of the tracer gas in the chamber where the partial pressure is smallest simultaneously increases.

The judiciously placed colorimetric detection layer 12 is then reached by the tracer gas, the partial pressure and concentration of said gas changing (decreasing or increasing) such that, depending on the arrangement, the concentration passes below or above the transition value. In all cases, the colorimetric detection layer 12 changes from the first color to the second color in response to the concentration of the tracer gas that reaches it passing above or below the transition value.

Thus, if the colorimetric detection layer 12 is of the first color, one can conclude that the first envelope/pouch stricto sensu 1 is of satisfactory integrity and therefore is suitable for receiving and protecting the biopharmaceutical product or device. In the context of the process which makes use of a pouch stricto sensu 1, such a first envelope/pouch stricto sensu 1 can be used, meaning first extracting it from the second envelope 8 then opening it to introduce the biopharmaceutical product or device.

Conversely, if the colorimetric detection layer 12 is of the second color, one concludes that the first envelope/pouch stricto sensu 1 is of unsatisfactory integrity and therefore is unsuitable for receiving and protecting the biopharmaceutical product or device. In the context of the process which makes use of a pouch stricto sensu 1, such a first envelope/pouch stricto sensu 1 must not be used and generally it is immediately set aside and destroyed.

The arrangement of the integrity/non-integrity indicator pouch 2 is first of all chosen so that the colorimetric detection layer 12 cannot be reached by the tracer gas located within the intermediate space 14 or within the first space 6 at a concentration beyond the transition value, when the first envelope/pouch stricto sensu 1 is of satisfactory integrity.

The arrangement of the integrity/non-integrity indicator pouch 2 is secondly chosen so that the colorimetric detection layer 12 must necessarily be reached by the tracer gas located within the intermediate space 14 or within the first space 6 at a concentration beyond the transition value, when the first envelope/pouch stricto sensu 1 is of unsatisfactory integrity.

Therefore the permeability or impermeability to the tracer gas of the colorimetric detection layer 12 and of the spacer means 11 is chosen so that the colorimetric detection layer 12 is in fact reached by the tracer gas located within the intermediate space 14 or within the first space 6 at a concentration beyond the transition value, when the first envelope/pouch stricto sensu 1 is of unsatisfactory integrity.

We will now describe several specific arrangements of the integrity/non-integrity indicator pouch 2; the specific arrangements described are provided solely as non-limiting examples.

In a first arrangement illustrated by FIGS. 3A, 3B and 3C, the colorimetric detection layer 12 is permeable to the tracer gas such that the tracer gas can reach it if the first envelope/pouch stricto sensu 1 is of unsatisfactory integrity, and it is an integral part of the wall 3, 4 of the first envelope/pouch stricto sensu 1, being located on the outer face 1a of said wall and within the intermediate space 14.

In a second arrangement illustrated by FIGS. 4A, 4B and 4C, the colorimetric detection layer 12 is permeable to the tracer gas such that the tracer gas can reach it if the first envelope/pouch stricto sensu 1 is of unsatisfactory integrity, and it is an integral part of the wall 3, 4 of the first envelope/pouch stricto sensu 1, being located on the inner face of said wall and within the first space 6.

In a third arrangement illustrated by the FIGS. 5A, 5B and 5C, the colorimetric detection layer 12 is permeable to the tracer gas such that the tracer gas can reach it if the first envelope/pouch stricto sensu 1 is of unsatisfactory integrity, and it is an integral part of the wall 3, 4 of the first envelope/pouch stricto sensu 1, being inserted into the thickness of the wall 3, 4, placed between its outer face 1a and its inner face 1b and also between the first space 6 and the intermediate space 14.

In a fourth arrangement illustrated by FIGS. 6A, 6B and 6C, the colorimetric detection layer 12 is an integral part of the wall 13 of the second envelope 8, being located on the inner face 8a and within the intermediate space 14.

In a fifth arrangement illustrated by FIGS. 7A, 7B and 7C, the colorimetric detection layer 12 is an integral part of the wall 13, being inserted into the thickness of the wall 13, placed between its inner face 8a and its outer face 8b. In this case, the layer 16 of the wall 13 of the second envelope 13 with the colorimetric detection layer 12 on one side and the inner face 8a of the second envelope 8 on the other side, is permeable to the tracer gas, such that the tracer gas can reach the colorimetric detection layer 12 of a first envelope/pouch stricto sensu 1 of unsatisfactory integrity.

In a sixth arrangement illustrated by FIG. 8A, the colorimetric detection layer 12 is an integral part of a porous layer of the spacer means 11, said layer being located nearer the inner face 8a of the second envelope (8).

In a seventh arrangement illustrated by FIG. 8B, the colorimetric detection layer 12 is an integral part of a porous layer of the spacer means 11, said layer being located nearer the outer face 1a of the wall 3, 4 of the first envelope/pouch stricto sensu 1. The tracer gas therefore does reach the colorimetric detection layer 12, as the spacer means 11 are porous i.e. permeable to the tracer gas.

In a variant of the sixth and seventh arrangements which is not represented, a colorimetric detection layer 12 and a porous layer of the spacer means 11 are structurally combined to form a single layer, instead of forming two separate layers associated with each other.

With these described functional or structural arrangements, it is possible to identify the integrity or non-integrity of a pouch stricto sensu 1 at any moment after its manufacture and at least immediately prior to its planned use.

This can be done in a certain, easy, and rapid manner, without requiring a bulky or complex dedicated device, or difficult or tricky operations, and without requiring specialized personnel exclusively dedicated to integrity verification, and without needing to conduct positive testing on the pouch to ensure its integrity, as its non-integrity is indicated automatically and therefore does not require positive testing of each pouch when the pouch is one of a plurality of pouches.

This identification is achieved by identifying the color of the colorimetric detection layer 12.

The second envelope 8 is designed to allow identifying from outside of itself whether the colorimetric detection layer 12 is of the first color or the second color. As indicated, such an identification can be done by a human observer from outside the integrity/non-integrity indicator pouch 2. For this purpose, the second envelope 8 can be, depending on the embodiments, transparent or translucent or may comprise a transparent or translucent window for observing the color of the colorimetric detector 12 positioned facing or near this window.

In one possible embodiment, illustrated by FIG. 1, it is additionally arranged so there is outer protective packaging 16 that houses the integrity/non-integrity indicator pouch 2, the first envelope/pouch stricto sensu 1 then being located within the second envelope 8.

The invention relates to the integrity/non-integrity indicator pouch 2 as described and as implemented.

The invention also relates to such an integrity/non-integrity indicator pouch 2 of satisfactory integrity, the colorimetric detection layer 12 being of the first color.

The invention also relates to a pouch stricto sensu 1 of satisfactory integrity, intended to receive and protect a biopharmaceutical product or device.

Such a pouch stricto sensu 1 of satisfactory integrity consists of the first envelope/pouch stricto sensu 1 extracted from an integrity/non-integrity indicator pouch 2 of satisfactory integrity, meaning its colorimetric detection layer 12 is of the first color.

The invention also relates to a method for creating an integrity/non-integrity indicator pouch 2 as described.

To begin with, one has available a first envelope/pouch stricto sensu 1, a second envelope 8 in which the second introduction means for introducing the first envelope/pouch stricto sensu 1 are in the open state, spacer means 11, the tracer gas, the colorimetric detection layer 12 which is an integral part of a wall 3, 4 of the first envelope/pouch stricto sensu 1 and/or of a wall 13 of the second envelope 8 and/or of the spacer means 11, as was described.

Then the first envelope/pouch stricto sensu 1 is introduced into the second space 9 of the second envelope 8 via the second introduction means in the open state, the spacer means 11 being placed between the wall 3, 4 and the wall 13 where they serve to fulfill their function of preventing the walls from occluding any openings as was described.

Then the tracer gas is introduced, into either the first space (6) or the intermediate space (14), at a partial pressure that is different from that of the intermediate space (14) or the first space (6), respectively, via the tracer gas introduction means 15 which are in the open state. These tracer gas introduction means 15 are then placed in the closed state.

The arrangement of the integrity/non-integrity indicator pouch 2 is chosen so that the colorimetric detection layer 12 cannot be reached or conversely will be reached by the tracer gas, as was described above, and the permeability or impermeability to the tracer gas of the colorimetric detection layer 12 and of the spacer means 11 is accordingly chosen so that the colorimetric detection layer 12 is in fact reached by the tracer gas when such is necessary.

The first envelope/pouch stricto sensu 1 and the second envelope 8 are closed at the end.

The invention also relates to a method for obtaining a pouch stricto sensu 1 of satisfactory integrity and therefore ready to receive and protect a biopharmaceutical product or device without any possible deterioration of the pouch stricto sensu 1 which would originate from the outside, such as contamination.

To begin with, there is an available integrity/non-integrity indicator pouch 2 as described.

At any desired moment after its production and at least immediately prior to the planned use of the pouch stricto sensu 1, it is determined whether the colorimetric detection layer 12 is of the first color or the second color.

If the colorimetric detection layer 12 is of the first color, the second extraction means, with which the second envelope 8 is equipped in order to extract the first envelope/pouch stricto sensu 1, are brought to the open state; the first envelope/pouch stricto sensu 1 is extracted from the second space 9 of the second envelope 8; and the first introduction means 7, with which the first envelope/pouch stricto sensu 1, considered to be of satisfactory integrity, is equipped in order to introduce the biopharmaceutical product or device, are brought to the open state in order to place the biopharmaceutical product or device within.

If, conversely, the colorimetric detection layer 12 is of the second color, the first envelope/pouch stricto sensu 1 is not used for placing a biopharmaceutical product or device within, as the first envelope/pouch stricto sensu 1 is considered to be of unsatisfactory integrity.

The process of making use of a pouch stricto sensu 1, which when of satisfactory integrity is intended for receiving and protecting a biopharmaceutical product or device, comprising initial operations at a point of manufacture, final operations at a point of use, and intermediate operations at one or more locations, is now described.

The process comprises the creation, at the point of manufacture, of an integrity/non-integrity indicator pouch 2 comprising a pouch stricto sensu 1, by the method described above.

The process also comprises the shipping of the integrity/non-integrity indicator pouch 2 from the point of manufacture to the point of use, including storage and handling operations if there are such.

Lastly the process comprises, at least at the point of use and before—particularly immediately before—extracting the first envelope/pouch stricto sensu 1 from the second envelope 8 in order to place the biopharmaceutical product or device within, the identification of whether the colorimetric detection layer 12 is of the first color or the second color.

It follows from the above description that if the colorimetric detection layer 12 is identified as being of the first color, the process then comprises using the pouch stricto sensu 1, considered to be of satisfactory integrity, to place the biopharmaceutical product or device within in order to receive and protect it.

Conversely, if the colorimetric detection layer 12 is identified as being of the second color, the process does not make use of the pouch stricto sensu 1, as it is considered to be of unsatisfactory integrity and unsuitable for receiving and protecting a biopharmaceutical product or device. The pouch stricto sensu 1 is set aside and usually destroyed.

Where applicable, the determination of whether the colorimetric detection layer 12 is of the first color or the second color is done concurrently with any intermediate storage, shipping, and handling operations.

The invention claimed is:

1. Integrity/non-integrity indicator pouch (2) intended for receiving and protecting a biopharmaceutical product or device, comprising:
   a first, inner, envelope (1) which is flexible, closed, fluid-tight, and of plastic material, comprising a wall (3, 4) delimiting a first space (6), forming a pouch stricto sensu (1) intended to receive the biopharmaceutical product or device, comprising first introduction means (7) and first extraction means for respectively introducing/extracting the product or device, said means being in the closed state,
   a second, outer, envelope (8) which is closed, fluid-tight, and of plastic material, comprising a wall (13) delimiting a second space (9) in which is located the first envelope/pouch stricto sensu (1), comprising second introduction means and second extraction means for respectively introducing/extracting the second envelope/pouch stricto sensu (1), said means being in the closed state, an intermediate space (14) thus being arranged in the second space (9) outside the first envelope/pouch stricto sensu (1), spacing means (11) placed between the wall (3, 4) and the wall (13) such that the inner face (8a) of the wall (13) does not occlude any integrity-impacting opening in the outer face (1a) of the wall (3, 4), at least one tracer gas, located either in the first space (6) or in the intermediate space (14), at a partial pressure that is different from that of the intermediate space (14) or of the first space (6), respectively, introduced into the first space (6) and/or the intermediate space (14) by tracer gas introduction means (15), now in the closed state, at least one continuous colorimetric detection layer (12) for detecting the tracer gas, responding to the concentration of tracer gas which reaches it by changing from a first color to a second and different color, being an integral part of a wall (3, 4) of the first envelope/pouch stricto sensu (1) and/or of a wall (13) of the second envelope (8) and/or of the spacer means (11), the arrangement of the walls (3, 4, 13) of the first envelope/pouch stricto sensu (1) and of the second envelope (8), the spacer means (11), the tracer gas, and the colorimetric detection layer (12), on the one hand, and the permeability or impermeability to the tracer gas of the colorimetric detection layer (12), and of the spacer means (11), on the other hand, being chosen so that the colorimetric detection layer (12) cannot be reached by tracer gas located in the intermediate space (14) or in the first space (6) at a concentration beyond the transition value, when the first envelope/pouch stricto sensu (1) is of satisfactory integrity, and so that the colorimetric detection layer (12) is an any case reached by tracer gas located in the intermediate space (14) or in the first space (6) at a concentration beyond the transition value, when the first envelope/pouch stricto sensu (1) is of unsatisfactory integrity, such that if the colorimetric detection layer (12) is identified as being of the first color, the first envelope/pouch stricto sensu (1) is considered to be of satisfactory integrity and suitable for receiving and protecting the biopharmaceutical product or device, whereas if it is identified as being of the second color, it is considered to be of unsatisfactory integrity and unsuitable for receiving and protecting the biopharmaceutical product or device.

2. Integrity/non-integrity indicator pouch (2) according to claim 1, wherein the spacer means (11) comprise at least one porous layer fully and functionally covering the outer face (1a) of the wall (3, 4) of the first envelope/pouch stricto sensu (1) and/or the inner face (8a) of the wall (13) of the second envelope (8) and/or the face of the colorimetric detection layer (12) facing the intermediate space (14).

3. Integrity/non-integrity indicator pouch (2) according to claim 2, wherein the spacer means (11) comprise at least one porous layer which either structurally covers the outer face (1a) of the wall (3, 4) of the first envelope/pouch stricto sensu (1) and/or the inner face (8a) of the wall (13) of the second envelope (8) and/or the face of the colorimetric detection layer (12) facing the intermediate space (14), or is placed within the intermediate space (14).

4. Integrity/non-integrity indicator pouch (2) according to claim 2, wherein either the tracer gas is in the first space (6) at a higher partial pressure than in the intermediate space (14), the colorimetric detection layer (12) changing from the first color to the second color in response to the concentration of tracer gas which reaches it rising above a transition value, or the tracer gas is in the first space (6) at a lower partial pressure than in the intermediate space (14), the colorimetric detection layer (12) changing from the first color to the second color in response to the concentration of tracer gas which reaches it falling below a transition value.

5. Integrity/non-integrity indicator pouch (2) according to claim 2, comprising one of the following characteristics:

a colorimetric detection layer (12) is permeable to the tracer gas and is an integral part of the wall (3, 4) of the first envelope/pouch stricto sensu (1), being located on the outer face (1a) and in the intermediate space (14), or located on the inner face (1b) and in the first space (6), or inserted within the wall (3, 4), between its outer face (1a) and its inner face (1b) and between the first space (6) and the intermediate space (14);

a colorimetric detection layer (12) is an integral part of the wall (13) of the second envelope (8), being either located on the inner face (8a) and in the intermediate space (14), or inserted within the wall (13), between the inner face (8a) and its outer face (8b), the layer (16) of the wall (13) of the second envelope (13) adjacent on one side to the colorimetric detection layer (12) and on the other side to the inner face (8a) then being permeable to the tracer gas;

a colorimetric detection layer (12) is an integral part of a porous layer of the spacer means (11) which is either located near the outer face (1a) of the wall (3, 4) of the first envelope/pouch stricto sensu (1), or is located near the inner face (8a) of the second envelope (8);

a colorimetric detection layer (12) and a porous layer of the spacer means (11) are structurally combined to form a single layer.

6. Integrity/non-integrity indicator pouch (2) according to claim 1, wherein either the tracer gas is in the first space (6) at a higher partial pressure than in the intermediate space (14), the colorimetric detection layer (12) changing from the first color to the second color in response to the concentration of tracer gas which reaches it rising above a transition value, or the tracer gas is in the first space (6) at a lower partial pressure than in the intermediate space (14), the colorimetric detection layer (12) changing from the first color to the second color in response to the concentration of tracer gas which reaches it falling below a transition value.

7. Integrity/non-integrity indicator pouch (2) according to claim 1, comprising one of the following characteristics:

a colorimetric detection layer (12) is permeable to the tracer gas and is an integral part of the wall (3, 4) of the first envelope/pouch stricto sensu (1), being located on the outer face (1a) and in the intermediate space (14), or located on the inner face (1b) and in the first space (6), or inserted within the wall (3, 4), between its outer face (1a) and its inner face (1b) and between the first space (6) and the intermediate space (14);

a colorimetric detection layer (12) is an integral part of the wall (13) of the second envelope (8), being either located on the inner face (8a) and in the intermediate space (14), or inserted within the wall (13), between the inner face (8a) and its outer face (8b), the layer (16) of the wall (13) of the second envelope (13) adjacent on one side to the colorimetric detection layer (12) and on the other side to the inner face (8a) then being permeable to the tracer gas;

a colorimetric detection layer (12) is an integral part of a porous layer of the spacer means (11) which is either located near the outer face (1a) of the wall (3, 4) of the first envelope/pouch stricto sensu (1), or is located near the inner face (8a) of the second envelope (8);

a colorimetric detection layer (12) and a porous layer of the spacer means (11) are structurally combined to form a single layer.

8. Integrity/non-integrity indicator pouch (2) according to claim 1, wherein the first envelope/pouch stricto sensu (1) is a 2D pouch.

9. Integrity/non-integrity indicator pouch (2) according to claim 1, wherein the first envelope/pouch stricto sensu (1) is a 3D pouch comprising two gussets (4).

10. Integrity/non-integrity indicator pouch (2) according to claim 9, wherein the spacer means (11) comprise at least one porous layer completely and functionally, and where necessary structurally, covering the outer face of the inside of the gussets (4).

11. Integrity/non-integrity indicator pouch (2) according to claim 1, comprising one or more of the following characteristics:
- the spacer means (11) comprise at least one porous layer which fully and functionally, and where necessary structurally, covers the first introduction means and the first extraction means for respectively introducing/extracting the biopharmaceutical product or device and the tracer gas introduction means of the first envelope/pouch stricto sensu (1);
- the spacer means (11) comprise at least one porous layer of fabric, nonwoven fabric, PE, PP, PTFE;
- a tracer gas is chosen from among the group comprising oxygen, carbon dioxide, and helium;
- one among the first space (6) or the intermediate space (14) contains tracer gas and the other among the intermediate space (14) or the first space (6) does not contain or substantially does not contain tracer gas;
- the second envelope (8) is such that it allows identifying from outside of itself whether the colorimetric detection layer (12) is of the first color or the second color;
- the second envelope (8) is flexible;
- it additionally comprises an outer protective packaging (17) which houses the second envelope (8) within which the first envelope/pouch stricto sensu (1) is located.

12. Integrity/non-integrity indicator pouch (2) of satisfactory integrity consisting of an integrity/non-integrity indicator pouch (2) according to claim 1 where the colorimetric detection layer (12) is of the first color.

13. Method for creating an integrity/non-integrity indicator pouch (2) according to claim 1, wherein:
- one provides a first envelope/pouch stricto sensu (1), a second envelope (8) in which the second introduction means for introducing the first envelope/pouch stricto sensu (1) are in the open state, spacer means (11), the tracer gas, the colorimetric detection layer (12) which is an integral part of a wall (3, 4) of the first envelope/pouch stricto sensu (1) and/or of a wall (13) of the second envelope (8) and/or of the spacer means (11),
- the first envelope/pouch stricto sensu (1) is introduced into the second space (9) of the second envelope (8) via the second introduction means in the open state, the spacer means (11) being placed between the wall (3, 4) and the wall (13) such that the inner face (8a) of the wall (13) does not occlude any integrity-impacting opening on the outer face (1a) of the wall (3, 4),
- the tracer gas is introduced into either the first space (6) or the intermediate space (14), at a partial pressure that is different from that of the intermediate space (14) or of the first space (6), respectively, via the tracer gas introduction means which are in the open state, then these introduction means are brought to the closed state,
- the arrangement is chosen so that the colorimetric detection layer (12) cannot be reached or conversely is necessarily reached by the tracer gas, as required, and the permeability or impermeability to the tracer gas of the colorimetric detection layer (12) and of the spacer means (11) is accordingly chosen so that the colorimetric detection layer (12) is in fact reached by the tracer gas when such is necessary,
- the first envelope/pouch stricto sensu (1) and the second envelope (8) being closed.

14. Process for making use of a pouch stricto sensu (1), which when of satisfactory integrity is intended for receiving and protecting a biopharmaceutical product or device, said process comprising:
- at a point of manufacture, initial operations consisting of manufacturing a pouch stricto sensu (1),
- at a point of use, final operations consisting of using the pouch stricto sensu (1) by placing the biopharmaceutical product or device within,
- intermediate storage, shipping, handling operations, at one or more locations, characterized by:
- the creation by the method according to claim 13, at the point of manufacture, of an integrity/non-integrity indicator pouch (2) comprising a first envelope/pouch stricto sensu (1),
- the shipping of the integrity/non-integrity indicator pouch (2) from the point of manufacture to the point of use, including storage and handling operations when there are such,
- and, at least at the point of use and before extracting the first envelope/pouch stricto sensu (1) from the second envelope (8) in order to place the biopharmaceutical product or device within, the identification of whether the colorimetric detection layer (12) is of the first color or the second color,
- if the colorimetric detection layer (12) is identified as being of the first color, the first envelope/pouch stricto sensu (1) is considered to be of satisfactory integrity and is used for placing the biopharmaceutical product or device within in order to receive and protect it,
- whereas if the colorimetric detection layer (12) is identified as being of the second color, the first envelope/pouch stricto sensu (1) is considered to be of unsatisfactory integrity and is not used for placing the biopharmaceutical product or device within.

15. Process according to claim 14, wherein the identification of whether the colorimetric detection layer (12) is of the first color or of the second color is done concurrently with intermediate storage, shipping, or handling operations.

16. Process according to claim 14, wherein the identification of whether the colorimetric detection layer (12) is of the first color or of the second color is done at the point of use immediately prior to extracting the first envelope/pouch stricto sensu (1) from the second envelope (8) in order to place the biopharmaceutical product or device within.

17. Method for obtaining a pouch stricto sensu (1) of satisfactory integrity and ready to receive and protect a biopharmaceutical product or device, wherein:
- one provides an integrity/non-integrity indicator pouch (2) according to claim 1,
- the colorimetric detection layer (12) is identified as being of the first color or the second color,
- if the colorimetric detection layer (12) is identified as being of the first color:
- the second extraction means, with which the second envelope (8) is equipped in order to extract the first envelope/pouch stricto sensu (1), are brought to the open state,
- the first envelope/pouch stricto sensu (1) is extracted from the second space (9) of the second envelope (8),
- and the first introduction means (7), with which the first envelope/pouch stricto sensu (1), considered to be of satisfactory integrity, is equipped in order to introduce the biopharmaceutical product or device, are brought to the open state in order to place the biopharmaceutical product or device within, whereas if the colorimetric detection layer (12) is identified as being of the second color, the first envelope/pouch stricto sensu (1) is considered to be of unsatisfactory integrity and is not used for placing a biopharmaceutical product or device within.

* * * * *